United States Patent [19]
Beecher

[11] 4,243,040
[45] Jan. 6, 1981

[54] EXTRACTING DEVICE FOR REMOVING OBJECTS FROM HUMAN BODY PASSAGES

[76] Inventor: William H. Beecher, 292 Boyd Ave., Elmhurst, Ill. 60126

[21] Appl. No.: 76,150

[22] Filed: Sep. 17, 1979

Related U.S. Application Data
[63] Continuation of Ser. No. 767,696, Feb. 11, 1977.

[51] Int. Cl.³ .............................................. A61B 17/00
[52] U.S. Cl. .................................. 128/328; 128/349 B
[58] Field of Search .................... 128/303 R, 328, 311, 128/276, 356, 349 B, 344, 348, 749; 27/24 A

[56] References Cited
U.S. PATENT DOCUMENTS

| | | | |
|---|---|---|---|
| 1,292,306 | 2/1919 | Beck | 111/71 |
| 1,612,697 | 12/1926 | Cecil | 128/328 |
| 1,902,418 | 3/1933 | Pilgrim | 128/350 R |
| 2,845,930 | 8/1958 | Brown | 128/348 |
| 3,050,066 | 8/1962 | Koehn | 128/349 B |
| 3,053,257 | 9/1962 | Birtwell | 128/349 B |
| 3,112,748 | 12/1963 | Colburn | 128/349 B |
| 3,433,214 | 3/1969 | Silverman | 128/772 |
| 3,827,437 | 8/1974 | Inaba | 128/328 |
| 3,866,599 | 2/1975 | Johnson | 128/6 |
| 4,024,873 | 5/1977 | Antoshiw et al. | 128/349 B |
| 4,072,146 | 2/1978 | Howes | 128/348 |

FOREIGN PATENT DOCUMENTS

| | | | |
|---|---|---|---|
| 454642 | 7/1928 | Fed. Rep. of Germany | 128/262 |
| 1092161 | 11/1960 | Fed. Rep. of Germany | 128/350 R |
| 2127125 | 6/1971 | Fed. Rep. of Germany | 128/328 |
| 1272412 | 8/1961 | France | 128/328 |
| 1509011 | 12/1967 | France | 128/328 |
| 887456 | 1/1962 | United Kingdom | 128/349 R |
| 123286 | 1/1959 | U.S.S.R. | 128/328 |
| 457471 | 3/1975 | U.S.S.R. | 128/328 |

Primary Examiner—Robert W. Michell
Assistant Examiner—Arthur S. Rose
Attorney, Agent, or Firm—Burmeister, York, Palmatier, Hamby & Jones

[57] ABSTRACT

Useful for removing kidney stones, gall stones and other objects from human body passages, the extracting device comprises a thin tubular rubber sleeve having its proximal and distal ends connected to the distal ends of outer and inner flexible tubes insertable into the body passage. The sleeve is inflatable by fluid pressure, supplied along the clearance space between the tubes to dilate the passage. The distal end of the sleeve is turned inside out and, when the sleeve is inflated, forms a soft annular flaring convex portion bulging beyond the distal end of the inner tube for sealing engagement with the stone, which is captured by suction, applied through the inner tube. Then, the inner tube is retracted, so that the suction pulls the stone within the sleeve while progressively turning the sleeve inside out around the stone to envelop the stone, for removal with the tubes.

20 Claims, 14 Drawing Figures

(a) STEP 1
PROCEDURE -

(b) STEP 2

(c) STEP 3

(d) STEP 4

(e) STEP 5

(f) STEP 6

EXTRACTING DEVICE FOR REMOVING OBJECTS FROM HUMAN BODY PASSAGES

This application is a continuation of my copending application, Ser. No. 767,696, filed Feb. 11, 1977.

This invention relates to an extracting device for removing kidney stones or other objects from the urinary tract or other passages of the human body.

One object of the present invention is to provide a new and improved extracting device which can easily be inserted into the ureters or other narrow passages of the human body, and will be capable of removing kidney stones and other objects in a highly effective and efficient manner.

A further object is to provide such a new and improved extracting device which will be capable of removing kidney stones and other similar objects from narrow passages of the human body, without scratching or otherwise injuring the walls of the passages.

To accomplish these objects, the present invention preferably provides an extracting device comprising an outer flexible tube which is insertable into a body passage, such as a ureter in the urinary tract, an inner flexible tube slidably received within the outer tube for free longitudinal sliding movement, and a thin highly flexible and limp sleeve connected between the insertable end of the outer tube and the corresponding end of the inner tube for insertion into the body passage. The sleeve is inflatable by compressed air or some other fluid transmitted along the clearance space between the outer and inner tubes. The inflation of the sleeve dilates the body passage, so as to loosen any kidney stone or the like which may be lodged in the passage. A pressure source and a control valve are preferably connected to the free end of the outer tube, for selectively supplying fluid pressure thereto so as to inflate the sleeve.

A vacuum source and a vacuum control valve are preferably connected to the free end of the inner tube, for selectively providing a vacuum or suction within the inner tube, to suck the kidney stone against the end of the inflated sleeve, so as to capture the kidney stone. The inner tube is then retracted relative to the outer tube, so that the kidney stone will be pulled into the confines of the sleeve. Simultaneously, the sleeve is preferably deflated so that the sleeve will enfold the kidney stone. The outer and inner tubes may then be withdrawn from the body passage, so as to remove the kidney stone or other object. The sleeve surrounds the kidney stone and prevents it from scratching or otherwise injuring the inner walls of the body passage.

The flexible inner and outer tubes are preferably made of a resinous plastic material, such as polyethylene, for example. An X-ray contrast medium is preferably incorporated into or coated upon the material of the outer or inner tube, so that an X-ray fluoroscope may be used to assist in inserting the outer tube into the ureter or other body passage. Alternately, the probe formed by the outer and inner tubes can be rendered visible on an X-ray fluoroscope by inserting a flexible metal wire within the inner tube.

The inflatable sleeve is preferably made of a thin elastic latex rubber material or the like.

A manipulator is preferably connected to the free ends of the outer and inner tubes, so that the operator can easily advance and retract the inner tube, relative to the outer tube, with the thumb and fingers of one hand. The other hand may then be employed to operate the control valves which regulate the air pressure and the suction.

The inflatable sleeve preferably has first and second reduced end portions which are stretched around and secured to the outer and inner tubes. The second end portion is preferably reentrant, in that it extends into the sleeve, so that the inflated sleeve will project endwise beyond the end of the inner tube. In this way, the inflated sleeve will be capable of forming a seal with the kidney stone or other object to be removed.

One or more auxiliary tubes may be inserted through the inner tube, to provide auxiliary communication with the body passage. The auxiliary tubes may be employed to supply various fluids to the body passage, such as air, a lubricant, or various medications. The auxiliary tubes may also be employed to withdraw mucus or other fluids from the body passage. An auxiliary tube having a plurality of tube elements or bores may be employed if desired.

Alternately, one or more auxiliary tubes may be inserted into the body passage along with the outer tube.

While the extracting device is particularly well adapted for removing kidney stones from the urinary tract, the extracting device may also be employed for removing gallstones, by inserting the extracting device through a drainage tube which has been installed during gallbladder surgery. The extracting device may also be employed to remove foreign objects from the respiratory tract or the esophagus.

Further objects, advantages and features of the present invention will appear from the following description, taken with the accompanying drawings, in which.

As just indicated, FIGS. 1–6 illustrate an extracting device 20 comprising an outer flexible tube or sheath 22 capable of being inserted into a narrow passage of the human body, such as one of the ureters. The outer tube 22 is sufficiently long to be inserted through the urethra and the bladder into one of the ureters, and along such ureter as far as possible toward the corresponding kidney. The diameter of the outer tube 22 is such as to fit snugly but comfortably into one of the ureters. The inflatable sleeve 28 can be made in various sizes to accommodate various sized objects to be removed. The inner tube 24 and the outer tube 22 can be sized accordingly. The outer tube 22 may be made of a resinous plastic material, such as polyethylene, for example. The tube 22 is sufficiently flexible to conform to the shape of the body passage, while being sufficiently stiff to provide for insertion of the tube without causing it to collapse.

The outer tube 22 may be inserted into one of the ureters with the aid of an auxiliary device such as a cystoscope and an X-ray system having a fluoroscope. Thus, the insertable portion of the extracting device 20 should preferably incorporate a material which is sufficiently opaque to X-rays to be visible on the fluoroscope. For this purpose, an X-ray contrast medium may be incorporated into the plastic material of the outer tube 22 or may be coated thereon. Alternately, a flexible metal wire may be inserted within the extracting device 20, as will be discussed below in greater detail. The wire is visible on the X-ray fluoroscope, and also may serve to stiffen the insertable portion of the extracting device 20, so that it will be easier to insert. Alternatively, a fiber optic device can be used for observing and guiding the probe during insertion.

Figures 1, 2, 3, 4, 5:
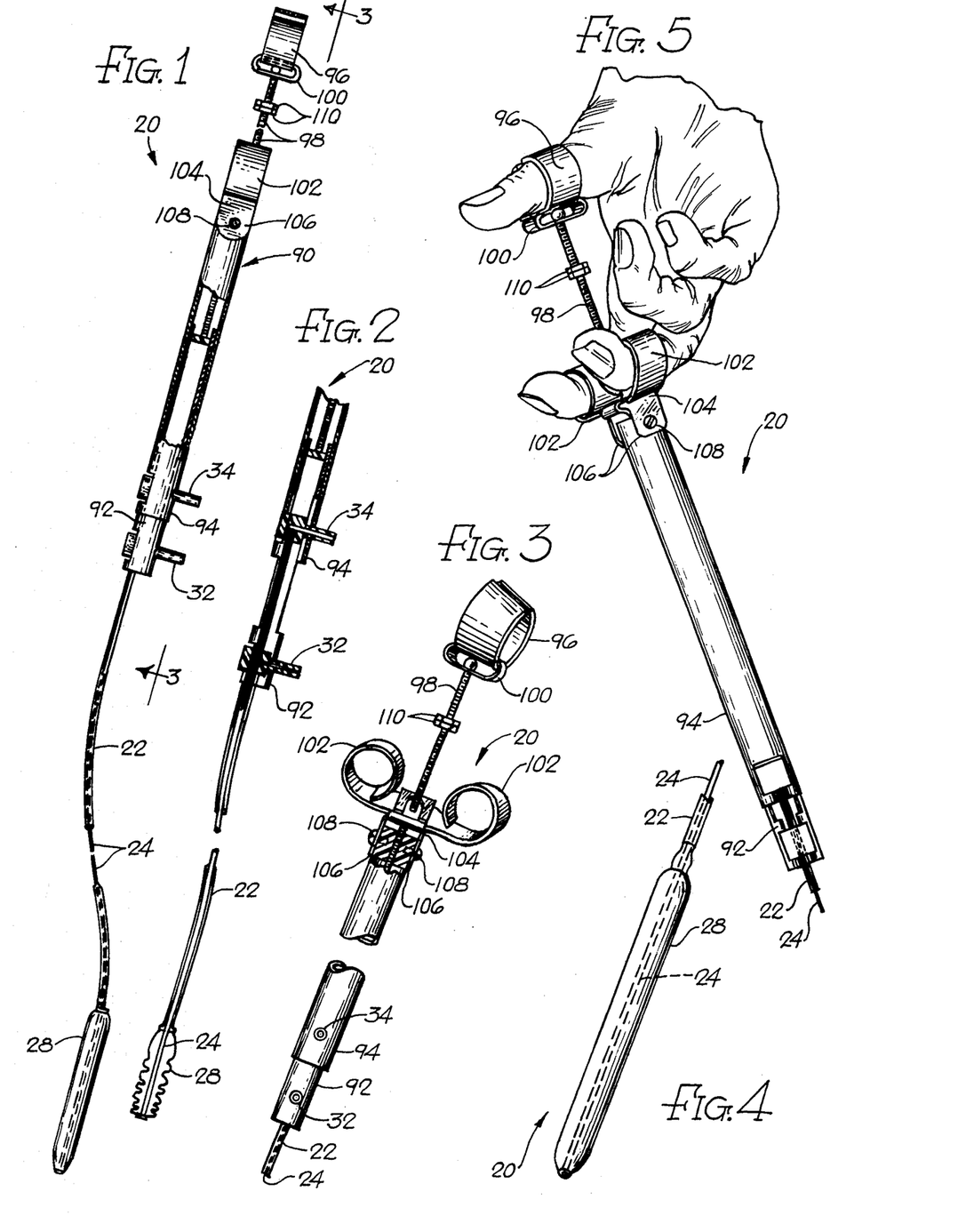
FIG. 1 is an elevational view of an extracting device to be described as an illustrative embodiment of the present invention, the view being partly in longitudinal section.
FIG. 2 is a fragmentary longitudinal section of the extracting device, showing the inflatable sleeve in a changed position.
FIG. 3 is a fragmentary elevation of the manipulator for the extracting device, the view being taken generally as indicated by the line 3—3 in FIG. 1.
FIG. 4 is a fragmentary perspective view showing the inflatable sleeve on the insertable end of the extracting device.
FIG. 5 is a fragmentary perspective view, showing the manipulator for the extracting device.
Figure 6:
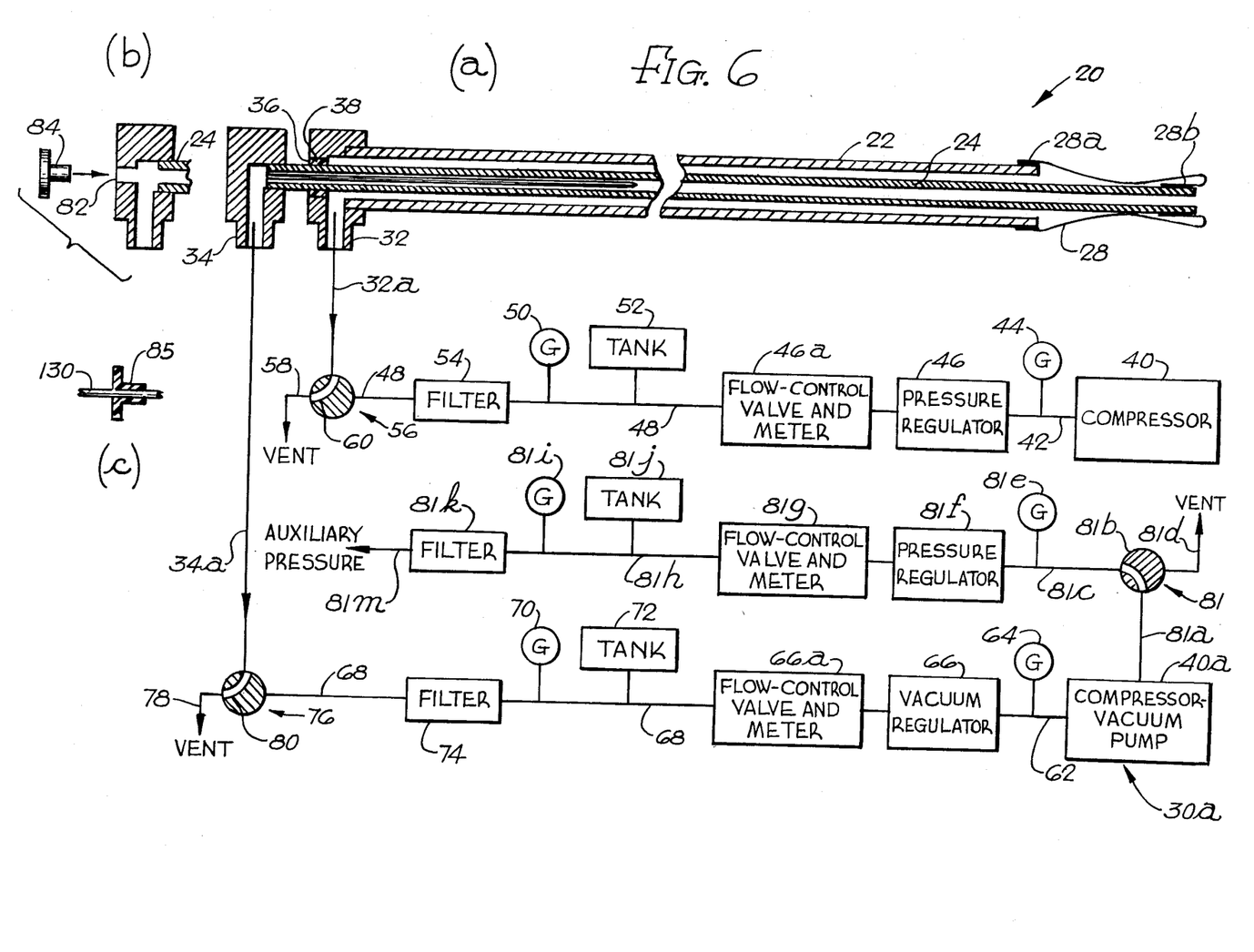
FIG. 6(a) is a fragmentary enlarged longitudinal section of the extracting device, the view being partly diagrammatic.
FIG. 6(b) is a fragmentary section corresponding to a portion of FIG. 6(a) and showing a modified construction.
FIG. 6(c) is a fragmentary section corresponding to a portion of FIG. 6(a) and showing a modified construction with a sliding seal used with a snare, wire or one or more auxiliary tubes, to permit full use of the device with the snare, wire or one or more auxiliary tubes in place.

As shown in FIG. 6, an inner flexible tube 24 is telescopically received within the outer tube 22, with an annular clearance space 26 therebetween for transmitting air or some other fluid under pressure. The inner tube 24 is freely slidable within the outer tube 22. As in the case of the outer tube 22, the inner tube 24 is preferably made of a resinous plastic material, such as polyethylene, for example. If desired, an X-ray contrast material may be incorporated into the material of the inner tube 24, or may be coated thereon so that the inner tube will be visible on an X-ray fluoroscope. Alternatively, a fiber optic device can be used for observing and guiding the probe during insertion. In addition to serving as a conduit for air or some other fluid, the inner tube 24 stiffens the outer tube 22 so that it may be inserted more easily into the body passage by the operator, without causing the outer tube 22 to collapse.

An inflatable sleeve or dilator 28 is connected between the distal or insertable end of the outer tube 22 and the corresponding or distal end of the inner tube 24. The sleeve 28 is thin, highly flexible and limp, and also is preferably elastic so as to be capable of stretching when inflated with compressed air or some other fluid. The sleeve 28 is preferably made of thin latex rubber or some other similar material. The thin rubber material may be similar to that employed for surgical rubber gloves and other thin rubber objects. A thin resinous plastic film material can also be used.

The thin flexible sleeve 28 has a first or proximal end portion 28a which is stretched around and secured to the insertable end of the outer tube 22, as by means of a suitable cement or adhesive. The sleeve 28 has a second or distal end portion 28b which is stretched around the insertable end of the inner tube 24 and is secured thereto, as by means of a suitable cement or adhesive. Any other suitable means, such as a tieing ring or collar, may be employed to secure the ends of the sleeve 28 to the ends of the tubes 22 and 24.

As shown in FIGS. 6(a) and 10(a), the distal end portion 28b of the flexible sleeve 28 is preferably reentrant or turned inside out, in that end portion 28b extends into the sleeve 28. With this construction, the sleeve 28 projects or bulges beyond the end of the inner tube 24, particularly when the sleeve 28 is inflated, as shown, for example in FIG. 7(b).

As shown in FIG. 6(a), the extracting device 20 preferably includes a system or means 30a for supplying air or some other fluid under pressure to the clearance space 26 between the outer and inner tubes 22 and 24, so as to inflate the thin flexible sleeve 28. The system 30a also preferably includes means for producing suction or a vacuum in the inner tube 24 to assist in capturing the kidney stone or other object which is to be removed from the body passage.

As shown in FIG. 6, the free or proximal end of the outer tube 22 is provided with a connector or fitting 32 to which a flexible hose 32a or the like may be connected, the hose being represented diagrammatically by a solid line. Similarly, the proximal end of the inner tube 24 is provided with a connector or fitting 34 to which a hose 34a or the like may be connected. As shown, the hoses 32a and 34a extend radially or at right angles to the outer and inner tubes 22 and 24. The inner tube 24 extends through an annular seal 36 mounted in an opening 38 in the fitting 32, such opening being coaxial with the outer tube 22.

The illustrated system 30a of FIG. 6 for selectively producing air pressure incorporates an air compressor 40 which supplies compressed air to a pressure line 42 to which a pressure gauge 44 may be connected. A pressure regulator 46 and a combination flow control valve and meter 46a are preferably connected between the high pressure line 42 and a low pressure line 48 to which another pressure gauge 50 may be connected. A storage tank 52 may also be connected to the low pressure line 48, if desired.

In this embodiment, a filter 54 and a control valve 56 are connected between the low pressure line 48 and the hose or conduit 32a which is connected to the end fitting 32 on the outer tube 22. The illustrated control valve 56 is of a three-way type, adapted to connect the interior of the outer tube 22 to either the pressure line 48 or a vent line 58 leading to the atmosphere. In the position of the valve 56 shown in FIG. 6(a), the outer tube 22 is connected to the vent line 58 by an internal passage 60 within the valve 56. It will be apparent that the valve 56 may be shifted to a position in which the internal passage 60 establishes a connection between the pressure line 48 and the interior of the tube 22. The pressure regulator 46 and the flow control valve and meter 46(a) may be adjustable so that the air pressure in the low pressure line 48 may be varied, as desired.

In the system 30a of FIG. 6(a), a combined compressor and vacuum pump 40a supplies vacuum to an output vacuum line 62, to which a vacuum gauge 64 may be connected. It will be realized that the compressor and the vacuum pump may be provided as two separate units, if desired. In this embodiment, a vacuum regulator 66 and a combination flow control valve and meter 66a are connected between the vacuum line 62 and a regulated vacuum line 68 to which another vacuum gauge 70 may be connected. A storage tank 72 may also be connected to the vacuum line 68 if desired.

A filter 74 and a vacuum control valve 76 are preferably connected between the regulated vacuum line 68 and the hose 34a which leads to the fitting 34 on the end of the inner tube 24. The control valve 76 may be of the three-way type and is shown in a position in which the interior of the inner tube 24 is connected to a vent line 78 by an internal passage 80 within the valve 76. It will be evident that the valve 76 can be shifted into a position in which the regulated vacuum line 68 is connected to the interior of the inner tube 24. The vacuum regulator 66 and flow control valve 66a may be adjustable so that the vacuum in the line 68 may be varied, as desired.

In the system 30a of FIG. 6(a), the combined compressor and vacuum pump 40a supplies pressure to an auxiliary pressure supply system 81, illustrated as comprising a compressor output pressure line 81a to which a control valve 81b may be connected. It will be realized that the compressor and the vacuum pump may be provided as two separate units if desired. The illustrated control valve 81b is of a three-way type, adapted to connect the compressor output pressure line 81a to either a high pressure input line 81c or a vent line 81d, leading to the atmosphere. In the position of the valve 81b shown in FIG. 6(a), the compressor output pressure line 81a is connected to the high pressure input line 81c. It will be apparent that the valve 81b may be shifted to a position in which the compressor output pressure line 81a is connected to the vent 81d. A gauge 81e may be connected to the high pressure input line 81c. A pressure regulator 81f and a combination flow control valve and meter 81g are preferably connected between the high pressure input line 81c and a low pressure line 81h to which another pressure gauge 81i may be connected. A storage tank 81j may also be connected to the low pressure line 81h if desired. In this embodiment, a filter 81k is connected between the low pressure line 81h and a hose or conduit 81m which is connected to the auxiliary tube or tubes 130 and 132, to be described in connection with FIGS. 9(a)-(d) and FIGS. 12 to 14.

FIG. 6(b) shows a modified construction of the fitting 34 having an axial opening 82 through which an auxiliary tube, a snare or a stiffening wire may be inserted into the inner tube 24. A plug 84 may be provided to close the opening 82 when not in use.

FIG. 6(c) shows another modified construction in which the plug 84 of FIG. 6(b) is replaced by a sliding seal or bushing 85 through which the auxiliary tube, snare or stiffening wire 130 may be inserted into the inner tube 24. The seal is inserted into the opening 82 in the fitting 32. The plug 84 may be used to close the opening 82 when the seal 85 is not in use.

As shown in FIGS. 1 to 5, a manipulator 90 is preferably connected to the free ends of the outer and inner tubes 22 and 24, to make it easy to advance and retract the inner tube 24 relative to the outer tube 22. By using the manipulator 90, the operator can advance and retract the inner tube 24 with the thumb and fingers of one hand, so that the other hand can be used to operate the pressure and vacuum control valves 56 and 76 of FIG. 6.

As illustrated in FIGS. 1 to 5, the manipulator 90 comprises a first member 92 which is telescopically slidable within a second member 94. The members 92 and 94 are connected to the outer and inner tubes 22 and 24, respectively. More specifically, the fitting or connector 32 on the free end of the outer tube 22 is mounted in the member 92, while the end fitting or connector 34 on the free end of the inner tube 24 is mounted in the member 94.

Finger and thumb rings are preferably provided on the telescopically slideable members 92 and 94. As shown, a thumb ring 96 is connected to the member 92 by means of a plunger rod 98. A swivel joint 100 is provided between the thumb ring 96 and the plunger rod 98, so that the thumb ring can be turned to an angle which is comfortable and convenient. The illustrated thumb ring 96 is made from a strip of sheet metal and can be bent to adjust the size of the thumb ring, as desired by the operator.

As shown, the member 94 is fitted with a pair of finger rings 102 which are also bent from a strip of sheet metal, so that the size of the rings 102 can easily be adjusted to suit the needs of the operator. The finger rings 102 are swingably mounted on the body member 94. For this purpose, the finger rings 102 are provided with a mounting member 104 having a pair of arms 106 which are swingably connected to the body member 94 by diametrically opposite pivots 108.

In the illustrated manipulator 90, two stop nuts 110 are mounted on the plunger rod 98, which is threaded to receive the stop nuts. It will be seen that the stop nuts 110 may be adjusted to limit the extent to which the plunger rod 98 may be depressed through the mounting member 104, which is apertured to provide a passage for the rod 98. In effect, the stop nuts 110 thereby provide an adjustment of the extent to which the inner tube 24 may be retracted relative to the outer tube 22.

Figure 7:
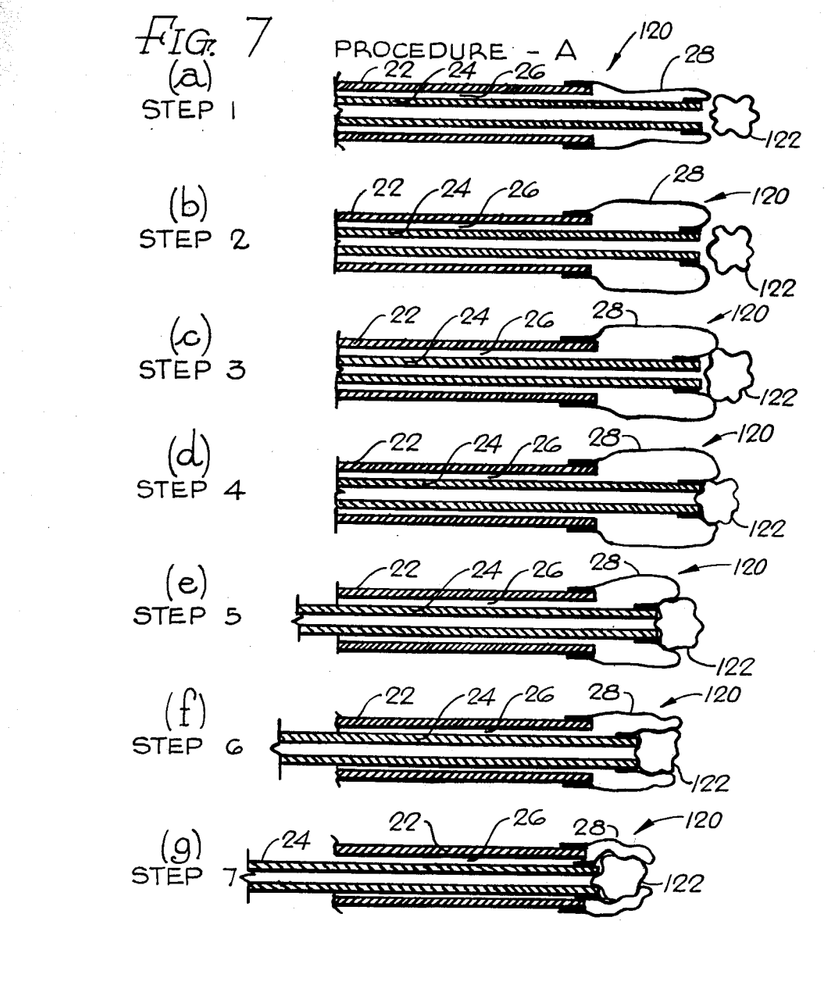
FIGS. 7(a)–(g) are a series of fragmentary sections showing successive steps in a procedure whereby the extracting device may be used to capture and enfold a kidney stone or some other object in a human body passage.
Figure 8:
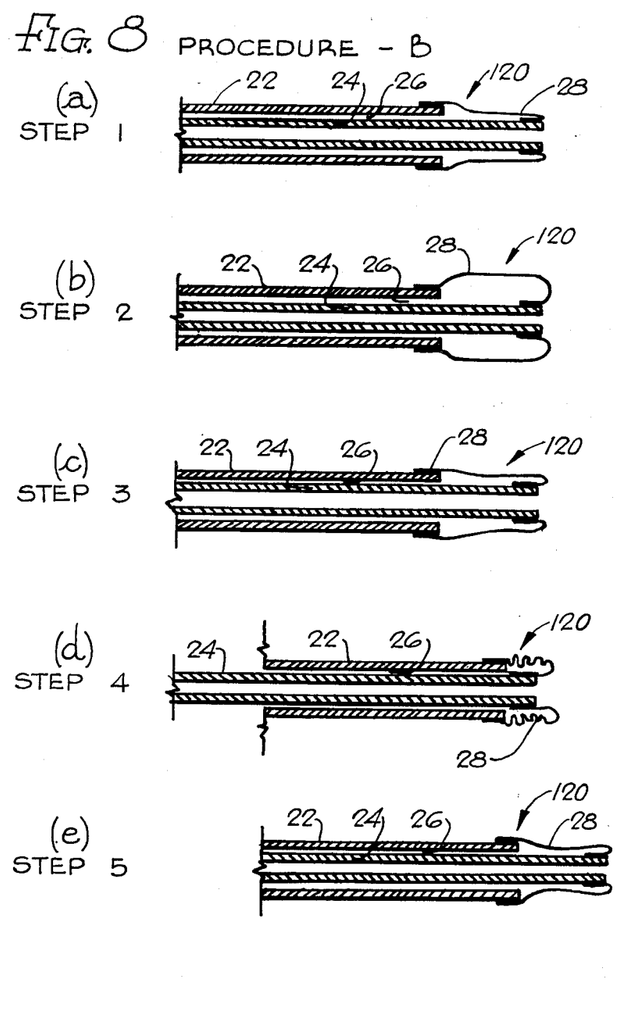
FIGS. 8(a)–(e) are a series of fragmentary sections showing successive steps in a procedure for advancing the insertable portion of the extracting device through a narrow body passage.

The operation of the extracting device 10 is illustrated in FIGS. 7 and 8, which should be taken in conjunction with FIGS. 1-6. The unit comprising the outer flexible tube 22, the inner flexible tube 24 and the inflatable sleeve 28 constitutes a probe 120 which can readily be inserted into the urinary tract of the human body for removing kidney stones. The diameter of the outer tube 22 is such as to fit snugly but easily into the urethra and either of the ureters. Specifically, the probe 120 is properly lubricated and is inserted through the urethra into the bladder, and then through the bladder into one of the ureters. An X-ray fluoroscope and a cystoscope may be employed advantageously to assist in inserting the probe 120 into either ureter. In order that the probe 120 may be clearly visible on the X-ray fluoroscope, the probe preferably incorporates an X-ray contrast material which is relatively opaque to X-rays. Such material may be incorporated into the plastic material of either the outer tube 22 or the inner tube 24, or both. Alternatively, the X-ray contrast material may be applied as a coating on either the outer tube 22 or inner tube 24, or both. For example, the X-ray contrast material may comprise a thin coating of a metal, such as gold, silver or aluminum. Another alternative is to insert a thin flexible metal wire into the inner tube 24, while the probe 120 is being inserted. The wire has the additional advantage of stiffening the probe 120. After the probe has been inserted, the wire can be removed.

FIGS. 7(a)-(g) show steps 1-7 of a procedure for capturing and removing a kidney stone 122 or some other similar object, which may be lodged in one of the ureters. As shown in FIG. 7(a), the probe 120 is inserted until it is close to the kidney stone 122. The sleeve 28 is then inflated, as shown in FIG. 7(b), by supplying compressed air through the clearance space 26 between the tubes 22 and 24. The compressed air is supplied by operating the compressed air control valve 56 to the position in which it transmits compressed air from the pressure line 48 to the fitting 32 on the free end of the outer tube 22.

The inflation of the sleeve 28 dilates the ureter to some extent, so as to dislodge or loosen the kidney stone 122. Suction is then applied to the inner tube 24, so as to suck the kidney stone 122 toward the end of the inner tube 24 and into engagement with the projecting end of the inflated sleeve 28, as shown in FIG. 7(c). The end of the thin rubber sleeve 28 forms a seal with the kidney stone 122, so that it is securely held against the end of the probe by the suction. As shown in FIG. 7(c), the projecting end of the inflated rubber sleeve 28 has an annular flaring portion bulging beyond the distal end of the inner tube 24 and covered convexly in longitudinal section, for sealing engagement with the kidney stone 122. The annular flaring curved portion of the sleeve 28, being made of thin rubber, is soft and pliable, and is capable of conforming to the shape of the kidney stone to form a seal therewith.

The inner tube 24 is then gradually retracted, while the sleeve 28 is simultaneously and gradually deflated, as shown in FIGS. 7(c)-(g), so that the kidney stone 122 is pulled within the confines of the sleeve 28. It will be seen that the deflated sleeve 28 enfolds the kidney stone 122, as shown to best advantage in FIG. 7(g), so that the sleeve 28 is interposed between the kidney stone 122 and the inner walls of the ureter.

The suction is applied to the inner tube 24 by operating the suction control valve 76 of FIG. 6, so that it establishes communication between the vacuum line 68 and the end fitting 34 on the inner tube 24. The suction is maintained while the probe 120 is withdrawn from the urinary tract. The kidney stone 122 remains a captive within the confines of the sleeve 28, so that the kidney stone is removed from the urinary tract. During the removal of the probe 120, the sleeve 28 prevents the kidney stone 122 from scratching or otherwise injuring the inner walls of the urinary tract.

FIG. 8 illustrates a procedure for using the inflatable sleeve 28 to assist in the insertion of the probe 120 into a narrow passage such as a ureter. In FIG. 8(a), the probe 120 has been inserted as far as possible with the sleeve 28 deflated. The sleeve 28 is then inflated, as shown in FIG. 8(b), so as to dilate the passage. Next, the sleeve 28 is again deflated, as shown in FIG. 8(c), and the outer tube 22 is immediately advanced, as shown in FIG. 8(d), while some of the dilation persists. The advancing movement of the outer tube 22 causes the sleeve 28 to collapse.

The inner tube 24 is then advanced within the outer tube 22, as shown in FIG. 8(e), so that the sleeve 28 is no longer collapsed. It will be seen that FIG. 8(e) is the same as FIG. 8(a), except that the probe 120 has been advanced. If further advancing movement is needed, the successive steps of FIGS. (a)-(e) are repeated. This may be done several times until the probe 120 has been fully inserted to the desired position in the ureter or other body passage.

Figure 9:
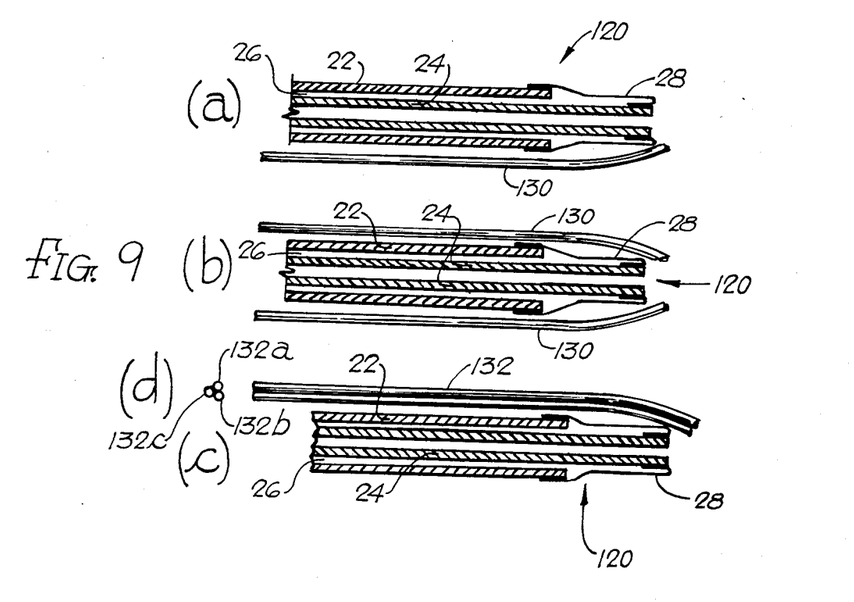
FIG. 9(a) is a fragmentary section showing the insertable portion of the extracting device, as employed in conjunction with an auxiliary tube adapted to be inserted into the body passage along with the extracting device.
FIG. 9(b) is a view similar to FIG. 9(a), but showing the extracting device in conjunction with two auxiliary tubes.
FIG. 9(c) is a view similar to FIG. 9(a), but showing the extracting device in conjunction with an auxiliary tube having three tube elements affording three individual passages.
FIG. 9(d) is an end view showing the triple auxiliary tube of FIG. 9(c).

In some cases, it may be desirable to insert an auxiliary tube 130, along with the probe 120, as shown in FIG. 9(a). The auxiliary tube 130 provides auxiliary communication with the ureter or other body passage and may be employed to convey various fluids to or from the body passage. For example, the auxiliary tube may be employed to carry air into the body passage, beyond the probe 120, so as to obviate or lessen the tendency of the suction, applied by the probe 120, to cause partial collapse of the walls of the body passage. When the auxiliary tube 130 is supplied with compressed air from the combination vacuum pump-compressor 40a of FIG. 6(a), the throughput of the closed system will provide the same amount of compressed air (volume measured as free air at atmospheric pressure) as the amount of air evacuated by the vacuum side of the pump (volume measured as free air at atmospheric pressure). The auxiliary tube 130 may also be employed to introduce a lubricating fluid into the body passage. A fluid medication can also be introduced into the body passage through the auxiliary tube 130. It is also possible to use the auxiliary tube 130 to withdraw mucus or other body fluids from the body passage.

As shown in FIG. 9(b), two or more auxiliary tubes 130 may be inserted into the body passage along with the probe 120, two such auxiliary tubes being shown in this view.

FIG. 9(c) shows a modified auxiliary tube 132 having a plurality of tube elements forming a plurality of individual auxiliary passages. As shown to best advantage in the cross section of FIG. 9(d), the auxiliary tube 132 has three tube elements 132a, b and c, which may be employed for simultaneously handling different fluids.

The auxiliary tubes 130 and 132 are preferably made of a flexible resinous plastic material, such as polyethylene, for example. The triple tube 132 may be formed by extrusion of the plastic material.

Figure 12:
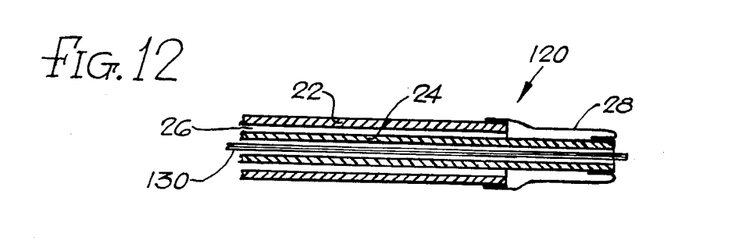
FIG. 12 is an enlarged fragmentary section showing the insertable portion of the extracting device in conjunction with a stiffening wire or auxiliary tube, inserted through the inner tube of the extracting device.
Figure 13:
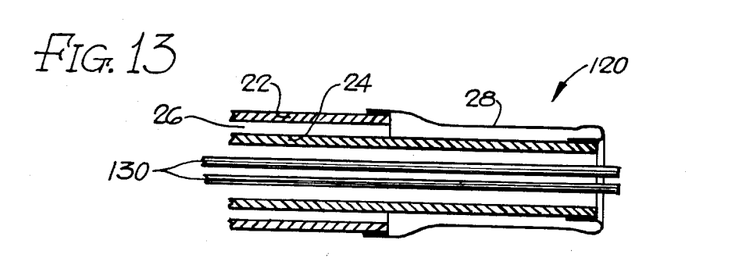
FIG. 13 is a fragmentary enlarged longitudinal section showing the extracting device in conjunction with a plurality of auxiliary tubes, inserted through the inner tube of the extracting device.
Figure 14:
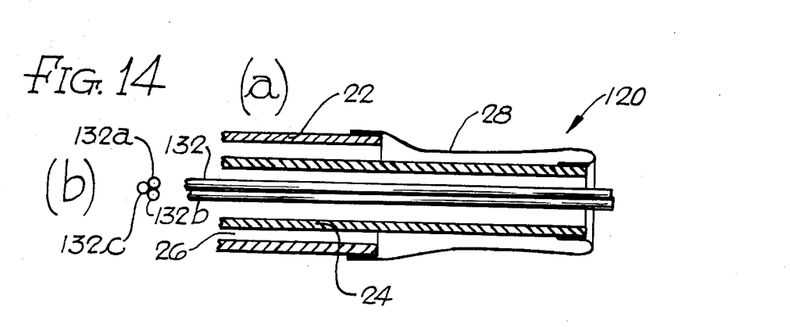
FIG. 14(a) is a fragmentary enlarged section of the insertable portion of the extracting device in conjunction with an auxiliary tube having a plurality of tube elements to afford a plurality of individual passages, the tube being inserted through the inner tube of the extracting device.
FIG. 14(b) is a fragmentary cross section of the auxiliary tube shown in FIG. 14(a).

FIG. 12 shows a modified arrangement in which the auxiliary tube 130 is inserted through the inner tube 24 of the probe 120. The auxiliary tube 130 may be inserted into the tube 24 through the sliding seal 85 of FIG. 6(c). As shown in FIG. 13, two or more of the auxiliary tubes 130 may be inserted through the inner tube 24, after being inserted into the tube through a suitable sliding seal.

FIGS. 14(a) and (b) show that the triple auxiliary tube 132 may be inserted through the inner tube 24 after being inserted through a suitable sliding seal. In all cases, the auxiliary tubes 130 and 132 may be inserted along the inner tube 124 either before or after the probe 120 is inserted into the body passage. The auxiliary tubes 130 and 132 may be removed from the inner tube 24 without removing the probe 120 from the body passage. The plug 84 may then be inserted in the connector.

It may also be considered that FIG. 12 illustrates insertion of a flexible metal wire within the inner tube 24. The element 130 may be regarded as the wire. As previously indicated, the flexible wire may be employed to stiffen the tubes 22 and 24 of the probe 120, or to absorb X-rays so that the probe 120 will be clearly visible on an X-ray fluoroscope.

Figure 10:
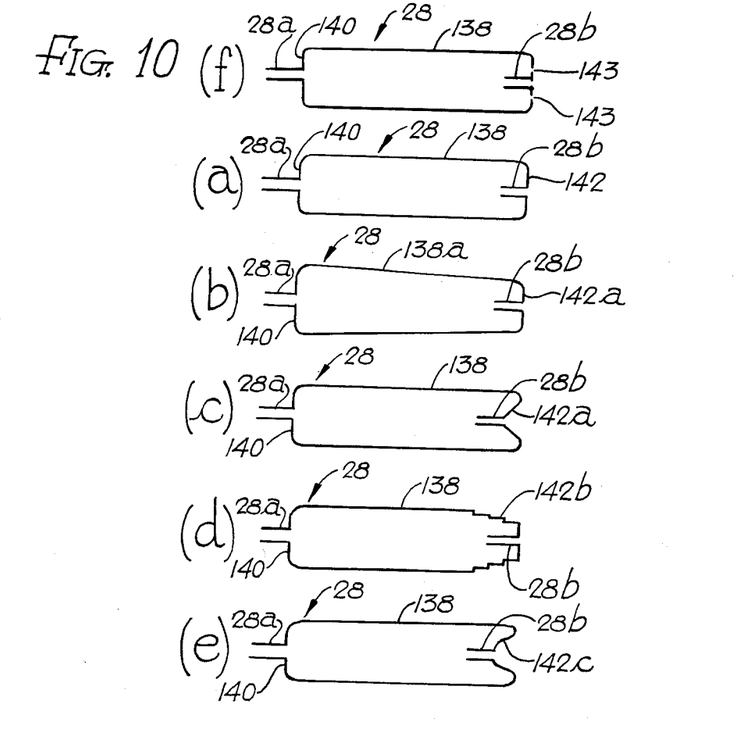
FIGS. 10(a)–(f) are a series of diagrammatic sections showing several alternative constructions of the inflatable sleeve.

FIG. 10 illustrates various alternative shapes for the inflatable sleeve 28. In FIG. 10(a), the sleeve 28 has a cylindrical sidewall 138 and radial endwalls 140 and 142. In FIG. 10(b) the sleeve has a tapered or frusto-conical sidewall 138(a).

In FIGS. 10(c), (d) and (e), the cylindrical sidewall 138 is employed, but the endwall 142 is modified. Thus, the sleeve of FIG. 10(c) has a re-entrant, tapered, frusto-conical endwall 142(a) which may be advantageous in some instances to assist in the enfolding of the kidney stone by the sleeve. In FIG. 10(d), the sleeve has a stepped endwall 142(b). In FIG. 10(e), the sleeve has a re-entrant endwall 142(c) which is concavely curved. This construction may be advantageous in some cases for capturing and enfolding kidney stones.

In FIG. 10(f), the inflatable seal or sleeve 28 has one or more holes 143 which may be either molded in or pierced. Air or fluid from the inflator supply will pass through the holes 143 so as to obviate or lessen the tendency of the suction applied by the probe 120 to cause partial collapse of the walls of the body passage. The various alternative shapes shown in FIGS. 10(b), (c), (d) and (e) may also be provided with one or more holes 143.

FIGS. 11(a)–(f) illustrate the successive steps of a procedure for using the probe 120 in conjunction with a snare 150 to assist in capturing and removing a foreign object, such as the illustrated kidney stone 122. The illustrated snare 150 comprises a capturing head or portion 154 and an operating portion or member 156, here shown as a flexible wire which is inserted through the inner tube 24, so as to be accessible to the operator at the free end of the probe 120. The wire 156 is freely slidable within the inner tube 24.

The capturing head 154 of the snare 150 may comprise a multitude of strands or filaments 158, made of a material such as tinsel, capable of entwining the kidney stone 122. The filaments 158 are in a form resembling a ball and are secured to the front end of the operating wire 156. The filaments 158 may be made of metal, a resinous plastic material, or any other suitable material.

Figure 11:
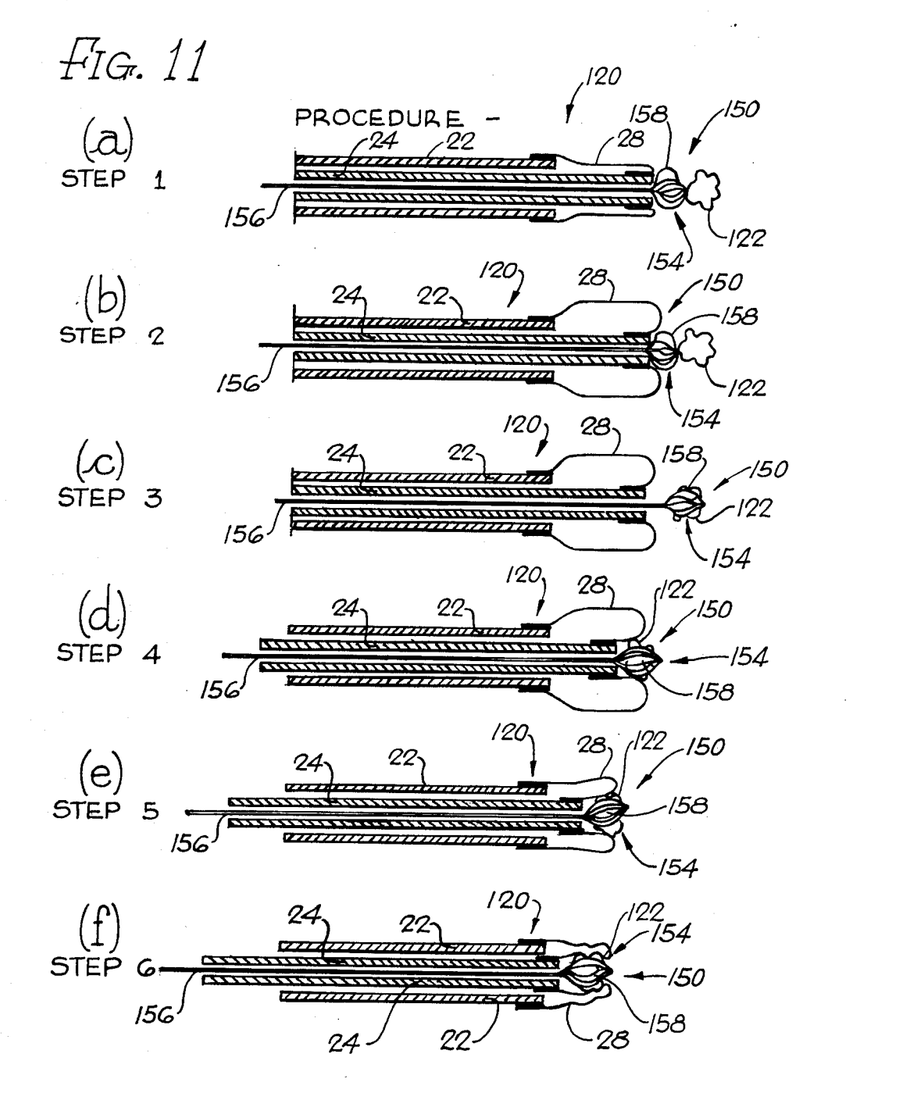
FIGS. 11(a)–(f) are fragmentary longitudinal sections showing the insertable portion of the extracting device in conjunction with a snare to assist in capturing a kidney stone or other object, the views showing successive steps of a procedure for capturing and enfolding the object.

In the procedure of FIGS. 11(a)–(f), the probe 120 is inserted into the ureter, or some other body passage, until the capturing head 154 of the snare 150 is as close as possible to the kidney stone 122, as shown in FIG. 11(a). The sleeve 28 is then inflated, as shown in FIG. 11(b), by supplying air or some other fluid under pressure to the interior of the outer tube 22. The inflation of the sleeve 28 tends to dislodge or loosen the kidney stone 122 from the walls of the ureter.

As shown in FIG. 11(c), the snare 150 is then advanced by moving the operating wire 156 through the inner tube 24. As the capturing head 154 is advanced, the filaments 158 become entwined around the kidney stone 122, as will be evident from FIG. 11(c). As the snare 150 is advanced, suction is preferably applied to the interior of the inner tube, so that the suction assists in the capture of the kidney stone 122.

The snare 150 is then retracted by moving the operating wire 156 within the inner tube 24, so as to bring the capturing head 154 and the kidney stone 122 as close as possible to the end of the inner tube. Meanwhile, suction within the inner tube 22 is maintained. Then, the inner tube 22 is gradually retracted, as shown in FIGS. 11(d)–(f), to draw the kidney stone 122 and the capturing head 154 of the snare 150 into the confines of the sleeve 28. Simultaneously, the sleeve 28 is gradually deflated, so that it will enfold the kidney stone 122 and the capturing head 154. The thin rubber sleeve 28 forms a seal with the kidney stone 122 and the capturing head 154, so that the suction effectively retains the kidney stone within the folds of the sleeve 28.

With the suction still maintained, the probe 120 may then be withdrawn from the body passage, to remove the kidney stone 122 or other object. The sleeve 28 is interposed between the kidney stone 122 and the walls of the body passage, so that neither the kidney stone nor the head 154 of the snare 150 will scratch or otherwise injure the walls of the body passage.

I claim:

1. An extracting device for insertion into a human body passage for removing foreign objects therefrom,
    said device comprising an outer flexible tube the distal end of which is insertable into a body passage,
    an inner flexible tube having a greater length than and slideably received within said outer tube for free longitudinal sliding movement with the distal end of said inner tube normally projecting beyond the distal end of said outer tube,
    said inner and outer tubes having clearance space therebetween for carrying fluid under pressure,
    a thin tubular highly distendable and limp sleeve having its proximal end portion connected to said distal end of said outer tube,
    said sleeve having a distal end portion which is inverted and is connected to the distal end of said inner tube for insertion into the body passage,
    said sleeve being otherwise free to expand upon inflation,
    said tubular sleeve having first and second tubular surfaces on opposite sides of said sleeve,
    said first surface facing inwardly at said proximal end portion of said sleeve,
    said inverted distal end portion of said sleeve being turned inside out with said second surface facing inwardly,
    said sleeve being inflatable by fluid transmitted along said clearance space to dilate the body passage,
    said sleeve when inflated having an annular flaring portion bulging beyond the distal end of said inner tube and curved convexly in longitudinal section for sealing engagement with a foreign object in the body passage, said annular flaring curved portion being soft, pliable and capable of conforming to the shape of the foreign object to effect a seal therewith, said inner tube being operative to transmit suction for capturing and holding the foreign object in sealing engagement with said annular flaring portion of said sleeve, and means for retracting said inner tube relative to said outer tube while the suction pulls the foreign object within the confines of said sleeve and said sleeve is progressively turned inside out around the foreign object to envelop the foreign object for removal with said tubes.

2. A device according to claim 1, in which said inner and outer tubes are made of a resinous plastic material.

3. A device according to claim 1, in which said sleeve is made of rubber.

4. A device according to claim 1, including manipulating means connected to the proximal ends of said tubes for advancing and retracting said inner tube relative to said outer tube.

5. A device according to claim 1, including manipulating means connected to the proximal ends of said inner and outer tubes for advancing and retracting said inner tube relative to said outer tube, said manipulating means including first and second telescopically movable members connected to said respective inner and outer tubes, said first and second members having finger receiving rings for use in manually moving said members.

6. A device according to claim 1, including means for selectively supplying fluid under pressure to the proximal end of said clearance space to inflate said sleeve.

7. A device according to claim 1, including means for selectively supplying suction to the proximal end of said inner tube.

8. A device according to claim 1, including first means for selectively supplying fluid under pressure to the proximal end of said clearance space for inflating said sleeve, and second means for selectively supplying suction to the proximal end of said inner tube.

9. A device according to claim 1, in which said proximal and distal end portions of said sleeve are of reduced diameters relative to the intermediate portion of said sleeve and are secured to the distal ends of said inner and outer tubes.

10. A device according to claim 1, in which said distal and proximal end portions of said sleeve are of reduced diameters relative to the intermediate portion of said sleeve and are secured to the distal ends of said inner and outer tubes, said reduced distal end portion of said sleeve extending within said sleeve for receiving the distal end of said inner tube whereby said sleeve projects beyond the distal end of said inner tube.

11. A device according to claim 1, including at least one auxiliary tube slideable within said inner tube to afford auxiliary communication with said body passage.

12. A device according to claim 1, including an auxiliary tube slidable within said inner tube to afford auxiliary communication with said body passage, said auxiliary tube including a plurality of individual tube elements.

13. A device according to claim 1, including at least one auxiliary tube extending along the outside of said outer tube and insertable in said body passage along with said outer and inner tubes to afford auxiliary communication with said body passage.

14. A device according to claim 13, in which said auxiliary tube has a plurality of individual tube elements.

15. A device according to claim 1, including a stiffening member slideably receivable in said inner tube for stiffening said inner and outer tubes to facilitate the insertion of said outer tube into the body passage.

16. A device according to claim 1, including a snare having an operating member slideable within said inner tube, said snare being operative to assist in capturing a foreign object in the body passage.

17. A device according to claim 1, including a snare having a thin flexible wire-like operating member slideably received in said inner tube, said snare having a capturing portion secured to said operating member and including a plurality of filaments disposed adjacent said sleeve to assist in capturing a foreign object.

18. An extracting device for insertion into a human body passage for removing foreign objects therefrom, said device comprising an outer flexible tube the distal end of which is insertable into a body passage, an inner flexible tube having a greater length than and slideably received within said outer tube for free longitudinal sliding movement with the distal end of said inner tube normally projecting beyond the distal end of said outer tube, said inner and outer tubes having clearance space therebetween for carrying fluid under pressure, a thin tubular highly distendable and limp sleeve having its proximal end portion connected to the outside of the extreme distal end of said outer tube, said sleeve having a distal end portion which is inverted and is connected to the outside of the extreme distal end of said inner tube for insertion into the body passage, said sleeve having a tubular wall with first and second tubular surfaces on opposite sides thereof, said proximal end portion of said sleeve being disposed with said first surface facing inwardly and engaged with the outside of said outer tube, said inverted distal end portion of said sleeve being turned inside out with said second surface facing inwardly and engaged with the outside of said inner tube, said sleeve being otherwise free to expand upon inflation, means for admitting fluid under pressure to said clearance space to inflate said sleeve and thereby dilate the body passage, said sleeve when inflated having an annular flaring portion bulging beyond the distal end of said inner tube and curved convexly in longitudinal section for sealing engagement with a foreign object in the body passage, said annular portion flaring outwardly directly from said inverted distal end portion of said sleeve and being soft, pliable and capable of conforming to the shape of the foreign object to effect a seal therewith, means for admitting suction to the proximal end of said inner tube to produce suction in the distal end thereof for capturing and holding the foreign object by sucking it into sealing engagement with said annular flaring portion of said sleeve, and means for retracting said inner tube relative to said outer tube while the suction pulls the foreign object within the confines of said sleeve and said sleeve is progressively turned inside out around the foreign object to envelop the foreign object for removal with said tubes.

19. An extracting device for insertion into a human body passage for removing foreign objects therefrom, said device comprising an outer flexible tube the distal end of which is insertable into a body passage, an inner flexible tube having a greater length than and slideably received within said outer tube for free longitudinal sliding movement with the distal end of said inner tube normally projecting beyond the distal end of said outer tube, said inner and outer tubes having clearance space therebetween for carrying fluid under pressure, a thin tubular highly distendable and limp generally cylindrical sleeve having its proximal end portion connected to the outside of the extreme distal end of said outer tube, said sleeve having a distal end portion which is inverted and is connected to the outside of the extreme distal end of said inner tube for insertion into the body passage, said sleeve having a tubular wall with first and second tubular surfaces on opposite sides thereof, said proximal end portion of said sleeve being disposed with said first surface facing inwardly and engaged with the outside of said outer tube, said inverted distal end portion of said sleeve being turned inside out with said second surface facing inwardly and engaged with the outside of said inner tube, said sleeve being otherwise free to expand upon inflation, means for selectively supplying fluid under pressure to said clearance space to inflate said sleeve and thereby dilate the body passage, said sleeve when inflated having an annular flaring portion bulging beyond the distal end of said inner tube and curved convexly in longitudinal section for sealing engagement with a foreign object in the body passage, said annular portion flaring outwardly directly from said inverted distal end portion of said sleeve and being soft, pliable and capable of conforming to the shape of the foreign object to effect a seal therewith, means for selectively applying suction to the proximal end of said inner tube to produce suction in the distal end thereof for capturing and holding the foreign object by sucking it into sealing engagement with said annular flaring portion of said sleeve, and means for manipulating the proximal ends of said inner and outer tubes to retract said inner tube relative to said outer tube while the suction pulls the foreign object within the confines of said sleeve and said sleeve is progressively turned inside out around the foreign object to envelop the foreign object for removal with said tubes, said tubular wall of said thin sleeve having a thickness which is substantially uniform throughout its extent between said proximal and distal end portions to provide for and facilitate the turning of said sleeve inside out to envelop the foreign object.

20. An extracting device for insertion into a human body passage for removing foreign objects therefrom, said device comprising an outer flexible tube the distal end of which is insertable into a body passage, an inner flexible tube having a greater length than and slideably received within said outer tube for free longitudinal sliding movement with the distal end of said inner tube normally projecting beyond the distal end of said outer tube, said inner and outer tubes having clearance space therebetween for carrying fluid under pressure, a thin tubular highly distendable and limp generally cylindrical rubber sleeve having its proximal end portion connected to said distal end of said outer tube, said sleeve having a distal end portion which is inverted and is connected to the extreme distal end of said inner tube for insertion into the body passage, said sleeve being otherwise free to expand upon inflation, said tubular sleeve having first and second tubular surfaces on opposite sides of said sleeve, said first surface facing inwardly at said proximal end portion of said sleeve, said inverted distal end portion of said sleeve being turned inside out with said second surface facing inwardly, said sleeve being inflatable by fluid transmitted along said clearance space to dilate the body passage, said sleeve when inflated having an annular flaring portion bulging beyond the distal end of said inner tube and curved convexly in longitudinal section for sealing engagement with a foreign object in the body passage, said annular portion flaring outwardly directly from said inverted distal end portion of said sleeve, said annular flaring curved portion being soft, pliable and capable of conforming to the shape of the foreign object to effect a seal therewith, said inner tube being operative to transmit suction for capturing and holding the foreign object in sealing engagement with said annular flaring portion of said sleeve, and means for retracting said inner tube relative to said outer tube while the suction pulls the foreign object within the confines of said sleeve and said sleeve is progressively turned inside out around the foreign object to envelop the foreign object for removal with said tubes, said tubular sleeve having a wall thickness which is substantially uniform throughout its extent between said proximal and distal end portions to provide for and facilitate the turning of said sleeve inside out to envelop the foreign object while maintaining the seal with the foreign object.

* * * * *